United States Patent [19]

Cooley et al.

[11] 4,130,403
[45] Dec. 19, 1978

[54] REMOVAL OF H₂S AND/OR CO₂ FROM A LIGHT HYDROCARBON STREAM BY USE OF GAS PERMEABLE MEMBRANE

[76] Inventors: T. E. Cooley; A. B. Coady, both of P.O. Box 5244, Station A, Calgary, Alberta, Canada, T2H 1X6

[21] Appl. No.: 821,459

[22] Filed: Aug. 3, 1977

[51] Int. Cl.² .......................................... B01D 53/22
[52] U.S. Cl. .......................................... 55/16; 55/68; 55/73
[58] Field of Search ........................ 55/16, 68, 73, 158

[56] References Cited

U.S. PATENT DOCUMENTS

| 2,947,687 | 8/1960 | Lee | 55/158 X |
| 2,966,235 | 12/1960 | Kammermeyer | 55/16 |
| 3,335,545 | 8/1967 | Robb et al. | 55/158 X |
| 3,415,038 | 12/1968 | Merten et al. | 55/16 |
| 3,422,008 | 1/1969 | McLain | 55/158 X |
| 3,534,528 | 10/1970 | Porter | 55/16 |
| 3,842,515 | 10/1974 | MacDonald et al. | 55/16 X |
| 3,884,801 | 5/1975 | Kesting | 55/158 X |

FOREIGN PATENT DOCUMENTS 2047359  5/1972  Fed. Rep. of Germany ............. 55/16

OTHER PUBLICATIONS

Brubaker et al., *Separation of Gases by Plastic Membranes*, Ind. & Eng. Chemistry, vol. 46, No. 4, Apr. 1954, pp. 733-739.
Envirogenics System Co. brochure titled, "*Spiral Wrap System of Reverse Osmosis Water Treatment*," dated 1976.

*Primary Examiner*—Robert H. Spitzer
*Attorney, Agent, or Firm*—Arnold, White & Durkee

[57] ABSTRACT

A method for removing H₂S and CO₂ from a natural gas stream involves the employment of a dried cellulose ester membrane having a permeability for H₂S and CO₂ of at least $10^{-8}$. A gas permeation process may also be used to produce a CO₂ rich stream from gas in gas reservoirs which contain a large amount of CO₂. The produced rich CO₂ stream may then be used in flooding processes for enchanced oil recovery.

17 Claims, 1 Drawing Figure

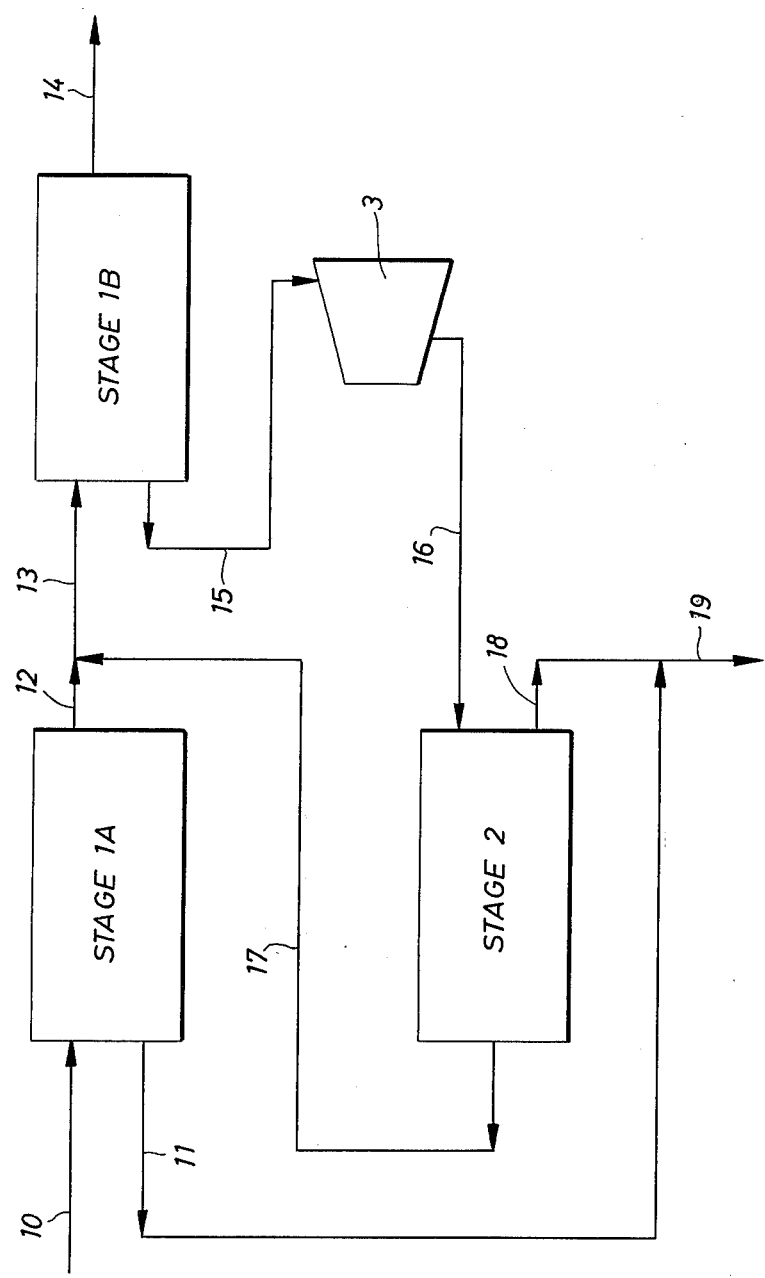

bg
REMOVAL OF H₂S AND/OR CO₂ FROM A LIGHT HYDROCARBON STREAM BY USE OF GAS PERMEABLE MEMBRANE

BACKGROUND OF THE INVENTION

Natural gas contains varying percentages of the following components: carbon dioxide, hydrogen sulfide, lower aliphatic hydrocarbons such as methane, ethane, propane, butanes, pentanes, hexanes and small amounts of aliphatic hydrocarbons having more than six carbon atoms, water, nitrogen, and trace amounts of gases such as mercaptans, carbonyl sulfide, helium and argon.

To be commercially acceptable, natural gas must meet stringent specifications with respect to heating value and the content of certain components. For example, a sufficient amount of hydrogen sulfide must be removed from the natural gas so that the gas product has an $H_2S$ concentration of no more than about $\frac{1}{4}$ to about $\frac{1}{2}$ grains per 100 standard cubic feet. Desirably, the carbon dioxide content of the gas product should be less than about two mole percent since higher concentrations can be corrosive. Also, carbon dioxide should be removed because its presence in a gas reduces that gas's heating value.

Acid gases such as $H_2S$ and $CO_2$ may be removed from hydrocarbon gas streams such as natural gas by many methods. These methods may be broadly classified as chemical reaction absorption, physical absorption and adsorption. The chemical reaction processes rely on a reversible chemical reaction and, in particular, use an absorbent which reacts with $CO_2$ and/or $H_2S$ in a contactor. The absorbent can be regenerated by use of a high temperature stripper. Chemical reaction processes include the amine processes such as the monoethanolamine (MEA) process, the diethanolamine (DEA) process and the sulfinol process which used a sulfolane (tetrahydrothiophene dioxide)-di-isopropanolamine (DIPA)-water mixture; the diglycolamine processes; the hot carbonate processes such as the Benfield, Girdler, Catacarb and Giammarco-Vetrocoke processes; and the iron-sponge processes which use a solution of quinone to convert $H_2S$ to sulfur.

The physical absorption processes rely on the affinity of certain chemicals for $CO_2$ and $H_2S$ and, basically, employ a contactor to remove the acid gases from the feed stream. Also, a stripper is used to separate the acid gases from the absorbent. These absorption processes include the patented Fluor solvent process which uses a refrigerated solvent consisting of anhydrous propylene carbonate; the Selexol process which may use the dimethylether of polyethylene glycol as a solvent alone or in combination with DIPA if low partial pressures of $H_2S$ in the product are required; the Sulfinol process which employs both a physical and a chemical solvent; and the Rectisol process which uses methanol as a solvent.

The adsorption processes are based on the unique adsorbent characteristics of certain minerals such as zeolitis. Generally, these adsorption processes are batch-type processes employing a molecular sieve. In operation the acid gas components of the feed gas stream are adsorbed on the surface of the mineral used and are subsequently removed from the mineral surface during a high temperature regeneration cycle. Molecular sieve processes can be designed to simultaneously dehydrate and sweeten natural gas streams.

All of the above-mentioned processes are not particularly attractive processes when the parameters often employed to evaluate various processes are reviewed. These parameters include: Capital cost, energy consumption, plant area requirements, manpower for operation and maintenance costs. The processes become more uneconomical for treating sour natural gas as the cost of the processes, evaluated with the above parameters, continue to increase. For example, on the North Slope of Alaska and on offshore platforms, the area available for process systems is extremely expensive and, hence, it follows that systems used at those locations should have small area requirements.

With regard to the high energy requirements of the above-mentioned systems, it is well known by those in the art that those systems are highly energy intensive. Molecular sieves, for example, must be heated to and held at approximately 600° F. during regeneration in order to remove all of the adsorbed material from the mineral surfaces. High energy input is required to achieve such temperatures. Further, it may be estimated that in the absorption processes three to seven standard cubic feet of acid gas can be removed in the absorber per each gallon of absorbent and from 1000 to about 1200 BTUs of heat per gallon of absorbent are required to remove the acid gas from the absorbent.

High capital investment and high operating costs of the above-described processes can be attributed, in part, to the wall thickness of the vessels required and the large number of pieces of equipment normally required. Normally, natural gas is sweetened at high pressures in order to minimize or avoid compression of the ultimate product.

Other processes have been used to separate one or more gaseous components from a gaseous mixture. In particular, membranes have been used for many years in gas separation. An excellent source of information concerning membrane technology is Hwang and Kammermeyer's MEMBRANES IN SEPARATION, which is Volume VII of a series entitled Techniques of Chemistry (Weissberger, ed. 1975).

Gas permeation may be defined as a physical phenomenon in which certain components selectively pass through a substance such as a membrane. Basically, a gas permeation process involves introducing a gas into one side of a module which is separated into two compartments by a permeable membrane. The gas stream flows along the surface of the membrane and the more permeable components of the gas pass through the membrane barrier at a higher rate than those components of lower permeability. After contacting the membrane, the depleted feed gas residue stream is removed from contact with the membrane via a suitable outlet on the feed compartment side of the vessel. The other side of the membrane, the permeate side, is provided with a suitable outlet through which the permeated gaseous components can be removed from contact with the membrane.

The purpose of a membrane in a gas permeation process is to act as a selective barrier, that is, to permit passage of some but not all components of a gaseous feed stream. Generally, in gaseous membrane separation processes, the separation is due to molecular interaction between gaseous components of the feed stream and the membrane. Because different components react differently with the membrane, the transmission rates (permeation fluxes) are different for each component. Hence, separation of different components can be effected.

Usually, permeation through a membrane involves both the diffusivity and solubility of the permeated component in and through the membrane. An exception to this occurs in microporous membranes wherein permeation proceeds purely on the basis of Knudsen (free molecular) diffusion, assuming the pores are sufficiently small. In actuality, the absorptive characteristics of gases may not be negligible and are usually temperature, pressure and surface flow dependent.

The membrane separation process involves several phenomena which occur as the more permeable components of the gaseous feed mixture pass over, through and out the other side of the membrane. Basically, mass transfer through a membrane proceeds by the sorption of a gaseous component on the feed side of the membrane, diffusion of that component through the membrane, and desorption of the component from the permeate side of the membrane. Each of these steps causes some resistance to the free flow of gaseous components through the membrane. Generally the diffusion step provides the most resistance to gas component transfer through the membrane barrier.

A gas permeation process may be comprised of one permeation module or a series of modules depending on the degree of separation desired. Many types of membranes, including cellulose esters and polymeric membranes such as silicone rubber, polyethylene, and polycarbonate, may be employed; however, the particular membrane used depends upon the type of separation sought to be effected. For example, if it is desired to separate helium from natural gas, a dried cellulose acetate membrane may be used since that membrane has a higher permeability for helium than for the hydrocarbons contained in natural gas.

For many years, cellulose ester membranes have been used for the desalination of salt water by reverse osmosis. A method of preparing cellulose acetate membranes is disclosed in U.S. Pat. No. 3,884,801. Typically, these membranes are water wet and do not exhibit good gas permeable properties in such condition. Years ago, it was discovered that if properly dried, these membranes could be used for gas separation. For example, U.S. Pat. No. 3,415,038 discloses several methods of drying cellulose acetate membranes. That patent also discloses that the dried cellulose acetate membranes can be used to separate helium from natural gas and to separate hydrogen from a mixture of hydrogen and carbon monoxide.

Other patents disclose the use of membranes in gas separation processes. For example, U.S. Pat. No. 3,842,515 discloses a method for drying cellulose acetate membranes and also discloses that these dried membranes may be used to separate helium from natural gas.

U.S. Pat. No. 2,947,687 disclosed that hydrocarbons may be separated according to type, molecular configuration, boiling point or molecular weight by using a non-porous membrane. It was further disclosed that the preferred membrane was an ethyl cellulose membrane having an ethoxyl content between 40 to 47 percent by weight.

In U.S. Pat. No. 3,335,545, it was disclosed that liquid or quasi-liquid barriers could be used for the separation of gaseous components from a mixture. In particular, it was disclosed that with a composite film of water and silicone the separation factor for $CO_2/O_2$ was 22–30 and about 20 for $CO_2/H_2S$. Further, it was disclosed that a composite film comprised of a 70 mil agar-agar-water gel film supported on a 3 mil silicone rubber film had the permeation constants of $10 \times 10^{-10}$ and $244 \times 10^{-9}$ cc. of gas, cm./sec., $cm^2$, cm.Hg. for oxygen and carbon dioxide respectively.

Another area of technology to which this invention has application is in enhanced oil recovery processes. After primary oil recovery from reservoirs, enhanced oil recovery has to be obtained by reservoir pressure maintenance and by waterflooding. Ultimate oil recovery, however, it quite limited by the application of these conventional methods. Today, other types of recovery processes are being utilized. These processes include steam flooding, chemical treatment (polymer flooding) and carbon dioxide flooding. Of these, carbon dioxide appears to have the best potential for obtaining the maximum oil recovery at a reasonable cost. The carbon dioxide flooding may be used alone or in conjunction with waterflooding.

Carbon dioxide flooding (CF) is known in the art to be quite useful in enhanced oil recovery processes. CF performs this task by many mechanisms including: (1) immiscible $CO_2$ drive; (2) miscible $CO_2$ drive; (3) hydrocarbon-$CO_2$ miscible drive; (4) solution gas drive; (5) hydrocarbon vaporization; and (6) multiple-contact dynamic miscible drive. In the L. W. Holm and V. A. Josendal, December 1974 paper published in the Journal of Petroleum Technology, the $CO_2$ properties which are important in effecting oil displacement are listed as follows: (1) $CO_2$ reduces oil viscosity; (2) $CO_2$ increases oil density; (3) $CO_2$ promotes swelling of oil; (4) $CO_2$ is highly soluble in water; (5) $CO_2$ in water has an acidic affect on limestone or carbonate rock by dissolving the rock and shrinking clays; (6) $CO_2$ vaporizes and extracts portions of crude oil; and (7) $CO_2$ is transported chromatographically through porous rock.

Although miscible flooding with $CO_2$ is becoming more popular, there are definite disadvantages. For example, the effectiveness of $CO_2$ is reduced in the presence of impurities such as methane and nitrogen. Apparently, the above mentioned impurities interfere with the dissolution of $CO_2$ in the crude oil. If the combined concentrations of methane and nitrogen in the $CO_2$ rich stream exceeds more than about 5 mole percent, the effectiveness of $CO_2$ appears to be severely reduced. Accordingly, an economical method for producing a rich $CO_2$ stream substantially free of impurities such as methane and nitrogen is required.

SUMMARY OF THE INVENTION

The instant invention provides a method for removing acid components from gaseous hydrocarbon streams such as natural gas. This invention also provides a method of producing a relatively pure stream of gaseous carbon dioxide which can be used in enhanced oil recovery processes such as miscible flooding. It has been discovered that cellulose ester membranes having a permeability constant for helium of at least $10^{-7}$ (measured at 100 psi) may be used for separating $H_2S$ and for $CO_2$ from hydrocarbon mixtures containing the same. Generally, such membranes will have permeability constants for $H_2S$ or $CO_2$ of approximately at least $10^{-8}$ (measured at 100 psi).

In the practice of the method of the instant invention, a gas stream from which selected components are to be separated is brought into contact with one side of a permeable membrane. The more permeable components of the feed gas will pass through the membrane to a much greater extent than other components. Hence, the desired separation can be effected. Following contact with the membrane, both the residue stream and the permeate gas stream are separately removed from contact with the membrane.

This separation process is a continuous one in which the feed stream is brought into contact with one side (feed side) of the membrane and the feed side pressure is maintained at a sufficient pressure higher than the permeate side of the membrane in order to provide a driving force for the diffusion of the most permeable components of the gaseous mixture through the membrane. Also, the partial pressure of the more permeable gaseous components is maintained at a higher level on the feed side of the membrane than on the permeate side by constantly removing both the permeate stream and the residue of the feed stream from contact with the membrane.

The membranes which may be utilized in the practice of this invention can be mounted and supported in a suitable module such as those which are normally used in reverse osmosis processes. Depending on the separation required, one module, at least two modules in parallel, or a series of modules arranged in any suitable fashion may be utilized.

In accordance with this invention, carbon dioxide and hydrogen sulfide can be separated from gaseous hydrocarbons or mixtures thereof in order to "sweeten" those streams, i.e., remove the acidic components. For example, natural gas stream containing acidic components can be contacted with a suitable membrane in order to remove the undesirable components, carbon dioxide and hydrogen sulfide.

In accordance with this invention, one module, at least two modules in parallel, or a series of modules containing suitable membranes and arranged in any suitable fashion may also be used to produce a substantially pure carbon dioxide stream from subterranean reservoir gases which are principally comprised of carbon dioxide. The resultant relatively pure carbon dioxide stream can then be used in enhanced oil recovery processes such as the miscible flooding of carbonate reservoirs.

The membranes which may be used in accordance with this invention should have a permeability constant of at least $10^{-8}$ for $CO_2$ or $H_2S$. Generally, such a permeability constant corresponds to a constant for helium of about $10^{-7}$. Preferably, the membranes which are utilized should be able to withstand high pressures of up to about 4000 psig. Although polymeric membranes having suitable permeability fluxes may be utilized, it is preferred to use a thin dried supported cellulose ester membrane.

Cellulose ester membranes and, in particular, cellulose acetate membranes have been utilized in reverse osmosis processes for the desalination of water for quite some time. These membranes when used for reverse osmosis do not exhibit good gas permeable characteristics; however, the membranes may be dried to remove water in accordance with any suitable process so that the resultant dried membrane has the desired permeability constant of at least $10^{-8}$ for carbon dioxide or hydrogen sulfide.

Cellulose ester membranes, either flat film or hollow fiber, may be utilized. These membranous materials may be selected from the group consisting of cellulose acetate, cellulose diacetate, cellulose triacetate, cellulose propionate, cellulose butyrate, cellulose cyanoethylate, cellulose methacrylate and mixtures thereof.

In addition to having the desired permeability constants for $H_2S$ and $CO_2$ the ratio of the permeability constant of the component having the lowest permeability of those components sought to be removed to the permeability of the component in the residue stream having the highest permeability and not sought to be removed from the mixture should be at least 5. For example, in a natural gas stream containing hydrocarbons such as methane, ethane, etc., and where a cellulose acetate membrane is utilized for permeation, it is known that methane has the highest permeability constant of the hydrocarbon constituents. Also, it is known that $H_2S$ has a higher permeability constant than $CO_2$. Therefore, in order to determine whether a separation of the acidic components, $H_2S$ and $CO_2$, from the hydrocarbon components can be effected, the separation factor for $CO_2/CH_4$ must be determined by dividing the permeability constant of $CO_2$ by the permeability constant of methane. If the separation factor is at least about five the separation can be effected. With lower separation factors, the separation of selected gaseous components from a mixture is not as feasible because more stages (modules) and, perhaps, compression of intermediate product streams are required.

Since the permeability constants of carbon dioxide and hydrogen sulfide increase approximately exponentially with an increase in pressure, a membrane which has a low permeability for either of those components can still be utilized for the separation of those components from a hydrocarbon mixture but the separation must take place at higher pressures.

Some hydrocarbon gases or reservoir gases may contain either $H_2S$ or $CO_2$ as acidic components. In these circumstances, cellulose ester membranes can still be used to remove the acidic component. Generally, the gaseous hydrocarbon streams may be pure components or mixtures of lower aliphatic hydrocarbons. In some cases, the gaseous hydrocarbon streams may contain small amounts of aromatic compounds such as benzene and toluene. Normally, the feed streams comprise lower aliphatic hydrocarbons or mixtures thereof. The hydrocarbons components generally will not have more than about eight carbon atoms. The hydrocarbons components may include methane, ethane, ethylene, propane, propylene, butanes, butylenes, etc.

When using a cellulose ester membrane and, in particular, a cellulose acetate membrane it has been found that in order for the membrane to retain good separation characteristics, the feed gas stream should be substantially water free. Accordingly, any suitable water removal process may be used which can reduce the moisture content of the feed gas stream to about 10 lbs/MMSCF.

It is preferred when practicing the method of the instant invention to pass the feed stream through a filter separator before contacting the feed stream with the membrane in order to remove particulate matter having a particle size greater than about one micron.

DESCRIPTION OF THE PREFERRED EMBODIMENTS

In accordance with this invention, acidic components, hydrogen sulfide and carbon dioxide, may be removed from a gaseous light hydrocarbon or a mixture of light hydrocarbons such as natural gas by the use of a suitable gas permeable membrane. In addition, a gas permeable membrane may be used to produce a relatively pure carbon dioxide gas which may be utilized in enhanced oil recovery processes such as the miscible flooding of carbonate reservoirs.

The light hydrocarbons from which $CO_2$ and/or $H_2S$ can be removed by the method of the instant invention include lower aliphatic hydrocarbons such as methane, ethane, propane, butanes, pentanes, hexanes and to a lesser extent, aliphatic hydrocarbons having less than about eight carbon atoms and mixtures thereof. Some feed streams may contain small amounts of aromatic components such as benzene and toluene.

Natural gas streams which can be treated in accordance with the instant invention typically contain at least about 2% carbon dioxide and about the same minimum concentration for $H_2S$. Some natural gases may contain up to about 98% $CO_2$ or 98% $H_2S$. Gases containing high concentrations of $CO_2$ cannot be economically processed by conventional processes to produce a substantially $CO_2$ rich stream such as one containing about 95% $CO_2$. Thus, the use of membrane technology is particularly attractive in those cases.

Although in the preferred embodiment, $CO_2$ and/or $H_2S$ can be separated from a natural gas stream containing the same, it should be apparent that the method of the instant invention may be employed in separating either or both of those acidic components from any gaseous hydrocarbon mixture natural or synthetic.

In gas separation processes employing permeable membranes, the gaseous mixture is brought into contact with one side of a permeable membrane and a sufficient positive pressure differential is maintained across the membrane such that the more permeable gaseous components of the mixture are driven from the feed side of the membrane to the permeate side. These more permeable components pass through the membrane at a higher rate than do other components of feed mixture which have lower permeabilities. Also, the partial pressure of the more permeable components is maintained at a higher level on the feed side of the membrane than on the permeate side by separately removing the residue of the feed stream and the permeate stream from contact with the membrane.

For example, in a preferred embodiment, $CO_2$ and $H_2S$ are removed from a hydrocarbon mixture such as natural gas. Preferably the membrane used is a thin dried supported cellulose ester membrane having a permeability constant of at least $10^{-8}$ (measured at 100 psi) for $H_2S$ or $CO_2$. In this separation the differential pressure across the membrane should be at least 100 psi and the partial pressures of $CO_2$ and $H_2S$ should be maintained at a higher level on the feed side of the membrane than on the permeate side. Preferably, the partial pressure of $CO_2$ and $H_2S$ in the permeate stream should be at most about 80% of the partial pressure of those same components in the feed stream.

Generally, during the separation process, the depleted feed gas (residue) stream and the permeate gas stream are separately and continuously removed from contact with the membrane. By doing this the desired partial pressure of the permeated components can be maintained. The depleted feed gas can then be fed to another module, or at least two modules in parallel, or a series of modules arranged in any suitable fashion for further separation of those components sought to be removed from the feed. Also, the permeate gas stream may be similarly treated in order to produce a product having a higher concentration of the more permeable components.

When removing acidic components from natural gas streams the residue stream is typically the desired product. However, the permeate stream may also be a desirable product. For example, when $H_2S$ and $CO_2$ are removed from natural gas, the permeate stream should consist of large quantities of $H_2S$ and $CO_2$. This permeate stream can be further processed by use of a suitable membrane to separate virtually all of the $H_2S$ from the $CO_2$ and thus produce two streams, one consisting essentially of $CO_2$ and the other consisting essentially of $H_2S$. Either of these streams may be used for an enhanced oil recovery process. Alternatively, the entire permeate stream with both $H_2S$ and $CO_2$ as constituents may be used in an enhanced oil recovery process.

The diffusion of gases through non-porous membranes involves a relatively complex mechanism comprising the sorption of certain gaseous components on the feed side of the membrane, the diffusion of those components through the membrane and the desorption of those components on the permeate side of the membrane. The term "non-porous" membrane is used since the separation mechanism involved with the membranes useful in practicing the method of the instant invention are controlled principally by solubility and diffusivity relationships. As distinguished, the separation mechanism in porous membranes is controlled primarily by molecular diffusion. Non-porous membranes do, in fact, have pores ranging in size from about 5 to about 10 angstrom. Unless otherwise stated, any reference to membranes in this application is to non-porous membranes.

The flow of gas through a permeable membrane involves a relatively complex procedure which may be defined by the following equation:

$$F = QA(P_H - P_L)/t$$

wherein
F is the gas flow rate through the membrane (permeate rate) cc;
A is the area of the membrane, cm$^2$;
$P_H$ is the pressure on feed side of the membrane, cm. Hg;
$P_L$ is the pressure on permeate side of the membrane, cm. hg.;
t is the membrane thickness, cm.;
Q is the permeability constant, $$(cc)(cm)/(sec)(cm^2)(cm.Hg.)$$

It should be apparent from the above relationship that the permeability constant for a particular gas is dependent upon the membrane area, the differential pressure across the membrane, the rate of diffusion of the gaseous component through the membrane and the thickness of the membrane. Obviously, the membrane should be as thin as possible in order to obtain the maximum amount of gaseous diffusion through the membrane. In practice, however, the membrane thickness is limited by the need to have a membrane free from defects such as pinholes and the need to have a membrane which can withstand pressures as high as about 4000 psig.

The permeability constant of a particular gas through a particular membrane may be determined experimentally by contacting the gas with a membrane of known area and thickness, recording the differential pressure across the membrane and measuring the rate of diffusion of the gas through the membrane. After the permeability constant for several components has been determined, the relative separation of the two gases can be determined. Generally, in order to separate on gaseous component from another, the ratio of the permeability constants of the more permeable component to the other component should be at least five. For example, when using a cellulose acetate membrane and when separating hydrogen sulfide and carbon dioxide from a hydrocarbon mixture such as natural gas, it is known that methane is the most permeable of the hydrocarbon constituents of natural gas and that $H_2S$ is more permeable than $CO_2$. Thus, to determine whether a separation of $H_2S$ and $CO_2$ from the hydrocarbon constituents of natural gas can be effected by using a particular membrane, the permeability constants of $H_2S$ and methane must be determined and the relative separation factor of $H_2S$ to methane calculated. If the factor is at least about five, then the separation can be economically made. Membranes having lower separation factors are not preferred since the separation of the components is not economically feasible.

In the preferred embodiment of the instant invention, cellulose ester membranes such as cellulose acetate, cellulose diacetate, cellulose triacetate, cellulose propionate, cellulose butyrate, cellulose cyanoethylate, cellulose methacrylate and mixtures thereof may be utilized. These membranes may be flat film or hollow fiber.

In the preferred embodiment, the cellulose ester membrane utilized should have a permeability constant for helium of at least about $10^{-7}$. Generally, this permeability corresponds to a permeability constant for $H_2S$ and $CO_2$ of at least about $10^{-8}$. These constants may be determined by as described above. Since the permeabilities of $H_2S$ and $CO_2$ are pressure dependent, the permeability constant for $H_2S$ and $CO_2$ of at least about $10^{-8}$ has reference to a constant measured at a differential pressure across the membrane of 100 psi. The permeability constant for helium remains relatively constant with changes in pressure.

Although it is preferred to use cellulose ester membranes in the practice of the instant invention, other membranes may be used. Of course, these membranes should have permeability constants for $H_2S$ or $CO_2$ of at least $10^{-8}$ (measured at 100 psi). In cellulose ester membranes, $H_2S$ has a higher permeability constant than $CO_2$ and it is thought that this relationship holds for other membranes as well. However, characteristics do vary from membrane to membrane. For example, a silicone rubber membrane may be employed in removing $CO_2$ and/or $H_2S$ from a hydrocarbon feed stream at low pressures but it should be understood that silicone rubber membranes have higher permeabilities for heavier hydrocarbon components than for light hydrocarbon components. Thus, care must be taken in calculating the separation factor in that or in a similar circumstance.

Cellulose ester membranes are asymmetric membranes which consist of a very thin but dense (non-porous) layer and a supporting sublayer of larger pore size. It is in the thin dense layer that the actual diffusion takes place. These membranes may have a thickness of from about $1 \times 10^{-6}$ inch to 1 mil. Thus, especially in high pressure separation processes,, the membrane should be supported by a suitable support such as a porous metal or a porous polymeric material. Of course, at higher pressures, the membrane would likely rupture without sufficient support.

Cellulose ester membranes are generally used for the desalination of salt water in a reverse osmosis process. These membranes do not exhibit good gas permeable characteristics unless they are dried. Methods for drying these membranes are disclosed in U.S. Pat. Nos. 3,415,038 and 3,842,515. The disclosures in those patents are incorporated herein by reference.

In the preferred embodiment, a cellulose ester membrane which is a bled of cellulose acetates and which is spirally wound in a module is used. The membrane and module are produced by Envirogenics Systems Company of El Monte, California. That company produces a membrane module useful in reverse osmosis processes. These same membranes and modules can also be used for gas permeation processes in accordance with the instant invention if the membranes are first dried. Envirogenics dries the membranes in accordance with a proprietary method and produce a membrane which has a permeability constant for carbon dioxide or hydrogen sulfide of at least $10^{-8}$ and has a corresponding permeability constant for helium of at least about $10^{-7}$.

The spiral wrap modules produced by Envirogenics consist of a cylinder within a cylinder arrangement wherein the membrane is wound around the inner cylinder before being placed in the outer cylinder or casing. The inner cylinder is made from a polymeric material which has a series of longitudinal perforations to which one end of the membrane is affixed. The remainder of the membrane is wrapped around the inner supporting cylinder and this inner cylinder wrapped with the membrane is disposed within the larger casing cylinder. The casing cylinder is enclosed on both ends by enclosing heads.

On one end, there are two orifices. Through one orifice the feed gas is introduced and as the feed gas passes over the membrane, the more permeable components of the gaseous mixture pass through the membrane and into and through the longitudinal perforations of the inner cylinder at a higher rate than the other components of the mixture. This permeate gas then flows through the inner cylinder in a direction countercurrent to that of the feed gas. The permeate gas is withdrawn through the same enclosing head as the feed; however, the permeate stream is withdrawn through the orifice connecting the inner cylinder with the encasing head orifice. That portion of the feed steam which does not permeate through and into the inner cylinder passes over the membrane and out the opposite side of the module through an orifice in the other encasing head.

The above described method of using the spiral wound modules is only one method by which the instant invention may be practiced. It should be understood that other flow schemes through the module may also be employed to practice the instant invention.

When acid components such as carbon dioxide and hydrogen sulfide are removed from a hydrocarbon mixture such as natural gas, one module, or at least two in parallel service, or a series of modules may be utilized to remove the acid components. For example, when one module is utilized, the pressure of the feed gas may vary from 25 to 4000 psig. The differential pressure across the membrane can be as low as about 10 psi or as high as about 2100 psi depending on many factors such as the particular membrane used, the flow rate of the inlet stream and the availability of a compressor to compress the permeate stream if such compression is desired. Differential pressures greater than about 2100 psi may rupture the membrane. A differential pressure of at least 100 psi is preferred since lower differential pressures may require more modules, more time and compression of intermediate product streams.

The operating temperature of the process may vary depending upon the temperature of the feed stream and upon ambient temperature conditions. Some membranes such as plastics and resins exhibit better permeability characteristics at higher temperatures; however, in the preferred embodiment, a cellulose acetate membrane is utilized and the permeability characteristics of that membrane are not substantially altered by a change in operating temperature. As a practical matter, the operating temperature may be maintained at ambient temperature. Generally, it is unnecessary to exceed temperatures of about 100° C.; however, it is possible to utilize higher temperatures if the circumstances require. The upper limiting temperature is thought to be that temperature at which the membrane deteriorates and no longer serves as a useful gas separator.

If more than one module are utilized, the inlet pressure to each module may vary depending on the pressure differential across the upstream membranes. In some circumstances compression of intermediate product streams may be required if higher permeation rates are desired.

As shown in FIG. 1, a schematic of a multiple stage membrane process, a multiple stage process may be utilized in accordance with this invention. The feed stream 10, is introduced into stage 1A at a pressure ranging from about 10 to 4000 psig. The permeate stream, 11, which contains a higher concentration of the more permeable components than the feed stream 10, is removed from stage 1A in a countercurrent fashion to the feed stream. For example, if stream 10 was a natural gas stream containing $H_2S$ and $CO_2$, permeate stream, 11, would contain a higher concentration of $H_2S$ and $CO_2$ than stream 10.

The residue gas, 12, is removed from stage 1A and is combined with the residue gas of stage 2, 17, to form the inlet stream, 13, to stage 1B. In stage 1B, a permeate stream 15, and a residue stream, 14, are obtained. The permeate stream may be fed to a compressor 3 which elevates the pressure of that stream sufficiently to drive it through stage 2 and to drive the residue stream, 17, through stage 1B. The inlet stream to stage 2, 16, is separated into a residue stream, 17, and a permeate stream, 18. The permeate stream from stage 2 may be combined with the permeate stream from stage 1A to form a combined permeate stream, 19. The combined permeate stream should have a high concentration of the more permeable components of the feed mixture.

If a sour natural gas feed stream consisting of 35 vol. % $H_2S$, 12 vol. % $CO_2$ and 53 vol. % $CH_4$ were fed to stage 1A at a rate of 100 mmscfd. it is calculated that the residue gas from stage 1B, indicated by reference numeral 14, would consist of approximately 1.1 volume percent $CO_2$ and 55.5 volume percent of $CH_4$ at a rate of approximately 56.6 mmscfd depending on the pressure of the feed stream and the particular membrane utilized. The acid gas (permeate) stream would consist of approximately 35 percent $H_2S$, 10.9 percent $CO_2$ and 2.5 percent. $CH_4$ and flow at the rate of approximately 43.4 mmscfd.

In the preferred embodiment, $H_2S$ and $CO_2$ are removed from a natural gas stream in order to meet pipeline or product specifications. Usually, hydrogen sulfide must be removed to a purity level of ¼ to ½ grain per standard cubic feet and carbon dioxide must also be removed to a level of about 2 mole % in the residue or product gas. When the method of the instant invention is used to produce a $CO_2$ rich stream for use in CF processes, the permeate stream should have at least about 95.0 vol. % $CO_2$.

It should be understood that in the preferred embodiment the natural gas stream may contain only one of the acidic components, $H_2S$ or $CO_2$, and in such a circumstance, a suitable membrane process in accordance with the instant invention may be employed to separate that component from the hydrocarbon mixture.

Further, it should be understood that the method of the instant invention may be used together with existing facilities to remove acid gas from a natural gas. For example, one membrane module or at least two modules in parallel or any combination of modules in series and parallel arrangements may be utilized in treating a feed gas to an existing sweetening facility. This pretreatment process can separate a substantial portion of the acid components from the natural gas. Thus, an increased quantity of gas may be treated by the existing unit or the unit may be used to treat the same quantity of gas for which it was originally employed. In this latter instance, if an absorption process was used as the existing unit, the flow of absorbent material could be reduced since a smaller quantity of "sour" components would have to be removed from the feed gas. With this reduced absorbent rate, the energy requirements for regeneration of the absorbent material would also be reduced.

The method of the instant invention may be useful in removing $CO_2$ from combustion or flue gases. Generally, these gases contain $O_2$, $N_2$, CO, $CO_2$ and uncombusted light hydrocarbons. For example, in the combustion of coal a typical flue gas stream should contain the following components in weight percent: $H_2O$–5.66; $CO_2$–20.59; $N_2$–69.19; $O_2$–4.42; $SO_2$–0.04; ash-$O_2$; oxides of $N_2$–0.05; $H_2$–0.01; and ammonia–0.001.

As previously indicated, cellulose ester membranes are preferred in the practice of the instant invention. It has been discovered that in order to function effectively, the feed gas to the cellulose ester membrane should be substantially water free. If water is not removed, experimentation has indicated that the permeability constants of all components increase but apparently the membranes are irreversibly damaged. In addition, the separation factor of carbon dioxide to methane or hydrogen sulfide to methane decreases to such a low value that the separation of the acid components from the hydrocarbon components is no longer commercially feasible. Accordingly, it is preferred to process the feed stream through a suitable moisture reduction system such that the feed to the membrane containing module has a moisture content of less than about 10 pounds per million standard cubic feet of gas. Any suitable moisture reduction process may be utilized. For example, a molecular sieve, silica gel, activated alumina or glycol contacting process may be used for this purpose.

In addition to the water removal step, the feed gas stream should be filtered in order to remove particulate matter larger than about 1 micron in size. Any suitable filter separator may be used for this purpose although it is preferred to use a filter supplied by PECO or Peerless Manufacturing. It is preferred to use a Peerless Series 31000 dry gas filter. In the preferred embodiment, this filtering step may be performed either before or after the water removal step. However, it is preferred to filter before water removal.

Some cellulose ester membranes supplied by Envirogenics have had permeability fluxes (Q/t) of about 5 to $7 \times 10^{-4}$ cc (STP) cm$^2$, sec, cmHg (at 100 psi) for carbon dioxide, about 3.5 to $9 \times 10^{-5}$ cc ((STP)/cm$^2$, sec, cm-Hg (at 100 psi) for methane and about $1-2\times10^{-3}$ cc(STP)/cm$^2$, sec, cm-Hg (at 10 psi) for helium. These values may vary depending on the drying technique used and on the procedures used to calculate the fluxes.

The membranes used in accordance with the instant invention should have a permeability constant of at least $10^{-8}$ (measured at 100 psi) for $H_2S$ or $CO_2$ and this corresponds to a He permeability constant of at least $10^{-7}$ (measured at 100 psi).

It should be understood that as the feed pessure is increased the permeability of $H_2S$ and $CO_2$ increase approximately exponentially while the permeabilities of methane and helium remain relatively unchanged. Accordingly, separations are more effective at higher pressures.

The preferred modules which may be used are the same as the standard ENRO "Ultra-high productive" modules sold by Envirogenics for reverse osmosis processes except the membranes used are dried by an Envirogenics proprietary method. Preferably, the permeate outlet of the module should be equipped with a safety relief valve set to relieve pressure at a preset value so that instruments downstream of the module are not damaged if the membrane ruptures and the instruments are exposed to the feed inlet pressure. Another precaution which must be taken is that when the module is first put into service the feed side pressure should be increased slowly to avoid rupturing the membrane. Also, the permeate stream should be equipped with a one way valve such as a non-return check valve so that flow through the membrane cannot be reversed.

The preferred modules are carbon steel pressure containers 4 inches in diameter and 42 inches long. Also, the modules may be equipped with Victaulic end caps and swagelok connections for the feed, permeate and residue stream connections.

Although the preferred modules are the spiral wound types previously described, it should be understood that other types of modules may be used. For example, plate and frame, tube type and hollow fiber type may be employed. Also, the spiral wrap modules may have one or more series of longitudinal perforations on the inner cylinder to which one side of a flat membrane can be affixed. Then, the flat membranes can be wound around the inner cylinder and the wound cylinder can be placed within the larger casing cylinder. Other types of spiral wound modules may be also be employed.

The following test is exemplary:

In this test a cellulose ester membrane and spiral wound module made by Envirogenics was utilized. The membrane was a blend of cellulose acetate, cellulose diacetate and cellulose triacetate. The module size was 36 × 4 inches O.D. The membrane was dried in the module by a two solvent step method similar to that disclosed in U.S. Pat. 3,842,515 except the solvent exchange was done at ambient temperature. The total membrane area was about 75 ft.$^2$.

A hydrocarbon gas as described in Table I was introduced into the module at the indicated conditions. The feed stream was saturated with moisture. The residue and permeate stream rate were recorded and samples of each were taken. The results of gas chromatograph analysis are recorded in Table I. These results illustrate that the dried cellulose acetate membrane can be utilized to remove $H_2S$ and $CO_2$ from a moisture saturated hydrocarbon feed stream.

TABLE 1

|  | Inlet | Residue | Permeate |
|---|---|---|---|
| psig | 830 | 825 | 20 |
| Temperature, °F | 87 | 87 | 82 |
| Flow rate, SCFH | 4,205 | 3,539 | 666 |
| Composition, mole % |  |  |  |
| $N_2$ | 2.87 | 2.92 | 1.94 |
| $CO_2$ | 12.25 | 9.00 | 36.15 |
| $H_2S$ | 0.09 | 0.17 | 0.89 |
| $C_1$ | 76.52 | 78.96 | 57.18 |
| $C_2$ | 4.90 | 5.22 | 2.57 |
| $C_3+$ | 3.37 | 3.73 | 1.27 |

In view of the preceding description, further modifications and alternative embodiments of the instant invention will be apparent to those skilled in the art. Accordingly, the preceding description is to be construed as explanatory and illustrative only and is for the purpose of teaching and enabling those skilled in the art to practice this invention.

While the preferred embodiment is to be understood to be the best mode presently contemplated, it is by no means the only embodiment possible. The scope of the invention is defined by the following claims and by any equivalent modifications and variations that fall within the true spirit of the invention.

What is claimed is:

1. A method for removing $H_2S$ and $CO_2$ from a gaseous hydrocarbon feed stream comprising $H_2S$ and $CO_2$ which comprises:
   exposing a first side of a thin dry supported cellulose ester membrane having a helium permeability constant of at least $10^{-7}$ and having a separation factor for $CO_2/CH_4$ of at least about 5 to said feed stream;
   maintaining said first side at a pressure of at least 100 psi greater than the permeate side of said membrane;
   separately removing the permeate stream and the residue of the feed stream from contact with said membrane to maintain a higher partial pressure of $H_2S$ and $CO_2$ on said first side than on said permeate side.

2. The method of claim 1 wherein said feed stream is substantially water free.

3. The method of claim 2 wherein said membranous material is selected from a group consisting of cellulose acetate, cellulose diacetate, cellulose triacetate, cellulose propionate, cellulose butyrate, cellulose cyanoethylate, cellulose methacrylate and mixtures thereof.

4. The method of claim 3 wherein said first side is maintained at a pressure of from about 100 to about 2100 psi greater than said permeate side.

5. The method of claim 4 wherein said gaseous hydrocarbon feed stream is natural gas.

6. The method of claim 5 wherein said membranous material is a mixture of cellulose acetate, cellulose diacetate and cellulose triacetate.

7. A method of removing $CO_2$ from a gaseous hydrocarbon feed stream comprising $CO_2$ which comprises:
   exposing a first side of a thin dry supported cellulose ester membrane having a helium permeability constant of at least $10^{-7}$ and having a separation factor for $CO_2/CH_4$ of at least about 5 to said feed stream;
   maintaining said first side at a pressure of at least 100 psi greater than the permeate side of said membrane;
   separately removing the permeate stream and the residue of the feed stream from contact with said membrane to maintain a higher partial pressure of $CO_2$ on said first side than on said permeate side.

8. The method of claim 7 wherein said feed stream is substantially water free.

9. The method of claim 8 wherein said membranous material is selected from the group consisting of cellulose acetate, cellulose diacetate, cellulose triacetate, cellulose propionate, cellulose butyrate, cellulose cyanoethylate, cellulose methacrylate and mixtures thereof.

10. The method of claim 9 wherein said first side is maintained at a pressure of from about 100 to about 2100 psi greater than said permeate side.

11. The method of claim 10 wherein said gaseous hydrocarbon feed stream is natural gas.

12. The method of claim 11 wherein said membranous material is a mixture of cellulose acetate, cellulose diacetate and cellulose triacetate.

13. A method of removing $H_2S$ from a gaseous hydrocarbon feed stream comprising $H_2S$ which comprises:

exposing a first side of a thin dry supported cellulose ester membrane having a helium permeability constant of at least $10^{-7}$ and having a separation factor for $CO_2/CH_4$ of at least about 5 to said feed stream;

maintaining said first side at a pressure of at least 100 psi greater than the permeate side of said membrane;

separately removing the permeate stream and the residue of the feed stream from contact with said membrane to maintain a higher partial pressure of $H_2S$ on said first side than on said permeate side.

14. The method of claim 13 wherein said feed stream is substantially water free.

15. The method of claim 14 wherein said membranous material is selected from a group consisting of cellulose acetate, cellulose diacetate, cellulose triacetate, cellulose propionate, cellulose butyrate, cellulose cyanoethylate, cellulose methacrylate and mixtures thereof.

16. The method of claim 15 wherein said first side is maintained at a pressure of from about 100 to about 2100 psi greater than said permeate side.

17. The method of claim 16 wherein said gaseous hydrocarbon feed stream is natural gas.

* * * * *